United States Patent [19]
Deac

[11] Patent Number: 5,344,442
[45] Date of Patent: Sep. 6, 1994

[54] CARDIAC VALVE

[75] Inventor: Radu Deac, Swarthmore, Pa.

[73] Assignee: Mures Cardiovasular Research, Inc., North Oaks, Minn.

[21] Appl. No.: 884,427

[22] Filed: May 15, 1992

Related U.S. Application Data

[63] Continuation-in-part of Ser. No. 701,099, May 16, 1991, abandoned.

[51] Int. Cl.⁵ ........................... A61F 2/24; A61F 2/76
[52] U.S. Cl. ..................................... 623/2; 623/900; 623/901
[58] Field of Search ..................... 623/2, 1, 3, 900, 901

[56] References Cited

U.S. PATENT DOCUMENTS

| | | | |
|---|---|---|---|
| 3,989,701 | 8/1975 | La Russa | 3/1.5 |
| 4,261,342 | 4/1981 | Duo | 128/1 |
| 4,790,844 | 12/1988 | Ovil | 623/2 |
| 4,960,424 | 10/1990 | Grooters | 623/2 |

FOREIGN PATENT DOCUMENTS

WO91/19465 12/1991 PCT Int'l Appl. .

OTHER PUBLICATIONS

Brewer III, *Prosthetic Heart Valves,* C. C. Thomas, 1969, Ch 58, pp. 820–831.
Merendino, *Prosthetic Valves in Cardiac Surgery,* C. C. Thomas, 1961, Ch 17, 19 and 21, pp. 307–339, 368–384, 402–425.
Braunwald et al, "Prosthetic Reconstruction of the Mitral Valve", 5 *Progress in Cardiovascular Diseases* 313–328 (Jan. 1963).
Berghuis et al, "Homotransplantation of the Canine Mitral Valve" 29 *Cardiovascular Surgery (Supp)* 47–53 (Apr. 1964).
Van der Spuy, "Completely Anatomical Autogenous Whole Mitral Valve", 19 *Thorax* 526–629 (1964).
O'Brien et al, "Homotransplantation of the Mitral Valve", 34 *The Australian and New Zealand Journal of Surgery* 81–88 (Nov. 1964).
Hubka et al, "Replacement of Mitral and Tricuspid Valves by Mitral Homograft", 51 *Journal of Thoracic and Cardiovascular Surgery* 195–204 (Feb. 1966).
Clarke et al, "The Fate of Preserved Homograft Pericardium and Autogenous Pericardium Within the Heart", 23 *Thorax* 111–120 (1968).
Holdefer et al, "An Experimental Approach to Mitral Valve Replacement With Autologous Pericardium", 55 *Journal of Thoracic and Cardiovascular Surgery* 873–881 (Jun. 1968).
Suzuki et al, "Mitral Valve Replacement With Transplant Valves", 60 *The Journal of Thoracic and Cardiovascular Surgery* 13–25 (Jul. 1970).
Love et al., "The Autogeneous Tissue Heart Valve: Current Status" *Journal of Cardiac Surgery,* vol. 6, No. 4, pp. 499–507 (1991).

*Primary Examiner*—Randall L. Green
*Assistant Examiner*—Elizabeth M. Burke
*Attorney, Agent, or Firm*—Kinney & Lange

[57] ABSTRACT

A cardiac valve comprises a plurality of flexible trapezoidal membranes, each having an edge joined to an edge of another of the membranes to form an unsupported frusto-conical body. The body has an oval end portion and a plurality of flexible flap portions integral with and extending from the end portions, the flap portions being formed by substantially parabolic scallops. The membranes are so sized, and the scallops are so positioned as to form flap portions of unequal size. The flexible membranes may be provided to the surgeon as separate membranes for construction of the artificial valve, or the valve may be provided to the surgeon as a complete unit. Alternatively, the surgeon may construct a valve using pericardium mapped and sized in accordance with the present invention.

18 Claims, 4 Drawing Sheets

CARDIAC VALVE

RELATED APPLICATIONS

This application is a continuation-in-part of application Ser. No. 07/701,099 filed May 16, 1991 now abandoned and assigned to the same assignee as the present application.

BACKGROUND OF THE INVENTION

This invention relates to cardiac valve replacement in heart surgery, and particularly to the replacement of the mitral valve.

Cardiac valve replacement is a relatively common procedure. However, in comparison with aortic, tricuspid and pulmonary valve replacement procedures, mitral valve replacement procedures have exhibited the poorest results in terms of morbidity and mortality. Under normal conditions, the mitral valve is exposed to the greatest pressure and stress during the cardiac cycle, with pressures often exceeding 150 mm Hg.

The mitral valve is generally a thin continuous, flexible membrane, strengthened by collagen fibers, surrounding the left atrio-ventricular ring having two indentations or commissures dividing it into two principal trapezoidal leaflets of unequal size: an anterior or aortic leaflet and a posterior or mural leaflet. The membrane at the junction of the two leaflets has sufficient length to form two auxiliary cusps located at each commissure. The membrane is attached to over two-thirds of the circumference of the atrio-ventricular ring and to the base of the aorta just below the aortic valve. The free ends of the leaflets are attached to chordae tendineae at the ventricular surface and in the regions of the commissures. The other end of the chordae connect to the papillary muscles, with each papillary muscle receiving chordae from both leaflets.

During diastole, a normal mitral valve will have a measured circumference between about 8.5 to 11 cm (for adult males) and 7.5 to 10.5 cm (for adult females). The calculated circularized valve orifice diastolic diameter is between about 27 and 35 mm (for adult males) and 23.8 and 33.4 mm (for adult females) and the calculated diastolic cross-sectional area is between about 5.75 and 9.62 sq. cm. for adult males and 4.5 and 8.77 sq. cm. for adult females. In cases of congestive heart failure, these dimensions enlarge, with the circumference of the adult male valve orifice reaching as high as about 12 cm, or greater and the adult female valve orifice reaching as high as about 11 cm.

The dimensions of the anterior leaflet are between about 1.9 and 3.2 cm in length and 2.5 and 4.5 cm in width for adult males, and 1.8 to 2.7 cm in length and 2.4 to 4.2 cm in width for adult females. The posterior leaflet has dimensions of between about 1.0 to 2.5 cm in length and 2.5 to 4.1 cm in width for adult males, and 0.8 to 2.4 cm in length and 2.3 to 3.6 cm in width for adult females. The chordae tendineae for both adult males and females is between about 1.3 and 3.2 cm. As the apical zones of the cusps correspond, the body of the anterior cusp lies opposite the base of the shorter posterior cusp. The chordae tendineae of the posterior cusp are inserted into almost the entire undersurface of the cusp, whereas those of the anterior cusp are inserted into a zone along its periphery. The remaining larger central triangular portion of the anterior cusp is thinner and more mobile than the marginal zone since its components are not directly limited by the chordae tendineae.

During systole a large portion of the anterior cusp billows toward the left atrium above the level of the base of the posterior cusp with about thirty percent of the anterior cusp co-apting with about fifty percent of the posterior cusp. The anterior cusp swings upwards and backwards. The swing of the anterior cusp is made possible by three cooperative actions: the absolute length of the anterior cusp and its chordae tendineae, the relative increase in length caused by the systolic approximations of bases of the papillary muscles toward the mitral ring, and the stretching of the papillary muscles by the interventricular pressure acting on the under surfaces of the cusps. Systolic excursions of the cusps are possible well beyond the normal requirements for valve closure due to the length of the cusps and the chordae tendineae and the extendibility of the papillary muscles. Consequently, the mitral valve has a large closing reserve. During diastole, the atrioventricular ring dilates and the valve leaflets descend to rapidly open the valve. The specific gravity of the leaflets is close to that of the blood so that as the ventricular chamber fills, the leaflets begin to float upward toward the annulus, initiating closure of the mitral orifice.

There is normally an excess of cusp tissue in relation to the size of the mitral ring. For example, for a mitral valve orifice area of about 7.9 sq. cm., a leaflet area of about 13.9 sq. cm. is available for closure. Thus, immediate and complete closure of the mitral valve takes place during systole with the ventricular contraction narrowing the mitral ring by about twenty-six to thirty-five percent (in comparison to its diameter during diastole.) The decrease in size of the mitral ring exposes less of the mitral valve surface to the burden of left ventricle systolic pressure. Thus, the annulus changes size from a relatively large opening during diastole and a smaller opening during systole.

The ideal valve substitute should be designed to reproduce as accurately as possible the normal flow pattern in the left side of the heart. The valve should have a large orifice, unrestrictive to a central free flow. It should operate at a low opening pressure without gradients across the valve, and be compatible with high outputs at exercise. The valve should exhibit rapid opening and closure throughout its entire range of pressures without regurgitant flow and without obstruction to the left ventricular output flow. The ideal valve substitute should be attached to the papillary muscles in such a manner as to maintain the valvular-papillary muscle continuity with a minimum of stress to thereby preserve the mechanics and contractural movement of the left ventricle. The valve should provide a uniform distribution of forces and stresses and avoid compressive, tensile or flexure stress during operation. The ideal valve should be constructed entirely of flexible tissue, without mechanical stents and the like. It should exhibit a long life, be durable, resistant to wear and resistant to degeneration, calcification and infection. It should provide normal heart sounds, without noise. It should produce no thrombo-embolic complications, and avoid trauma to blood elements. It should function normally as the left ventricle changes in size. The ideal valve should be easy and reliable to produce and implant.

Mitral valve replacements have not been altogether successful in the past because they have not fully taken into account all of the structural and functional characteristics of the normal mitral valve, including the dynamically changing structure of the mitral ring between systole and diastole, the large inflow orifice, excess leaflet tissue for closure, wall continuity between the mitral ring, papillary muscles and left ventricle, and the other factors mentioned above. Mechanical and bioprosthetic valves have not been altogether successful, because such valves do not have an adequately long life and do not fully simulate the action of a natural valve due to the rigidity of the structure and lack of support to the papillary muscles. Rigid mitral rings and supports do not simulate the physiologic sphincter-like contraction of the natural mitral ring during systole. Patients receiving mechanical valves require anti-coagulant therapy and risk the occurrence of thromboembolic phenomena. Hence, re-operation is necessary in many cases employing mechanical and bioprosthetic valves.

To overcome the problems of mechanical and bioprosthetic valves, many attempts have been made to construct a bicuspid mitral valve formed of entirely an unsupported tissue. However, most of the earlier unsupported valves did not fully account for the factors mentioned above.

SUMMARY OF THE INVENTION

In accordance with the present invention, a cardiac valve comprises a plurality of flexible trapezoidal membranes, each having an edge joined to an edge of another of the membranes to form an unsupported frustoconical annular body. The annular body has a ring-shaped end portion and a plurality of flexible flap portions integral with and extending from the ring-shaped end portion, the flap portions being formed by substantially parabolic scallops. The membranes are so sized, and the scallops are so positioned that the flap portions are of unequal size. For a bicuspid mitral valve with two such flap portions, the smaller flap portion forms the posterior leaflet and the larger flap portion forms the anterior leaflet. At least one junction between adjacent membranes is located along the length of each flap portion to simulate tendons and fibers in the native valve.

In one form of the invention, the flexible membranes are provided as individual trapezoidal membranes unjoined to others. When flat, each membrane has a rim portion between opposite edges, with an elliptic scallop at the end opposite the rim portion. The membranes are selected on the basis of various measurements of the excised valve, primarily (i) the circumference of the annulus, and (ii) the distance between the annulus and the tips of the papillary muscle. The membranes and/or scallops are so sized as to form leaflets of different sizes, as one serves as the anterior leaflet and the other as the posterior leaflet. The surgeon sutures the edges of the two membranes to form the annular cardiac valve, and attaches the apical ends of the flap portions formed at the junction of the two membranes to the chordae tendineae at the papillary muscles. The cylindrical rim is then attached to the mitral annulus.

In another form of the invention, the membranes are provided in a tissue form with the two membranes already joined by suture.

One feature of the present invention resides in the provision of a technique for selecting and orienting membrane material for use in forming the individual trapezoidal membranes.

Another feature of the present invention resides in the provision of a kit comprising a plurality of cutting dies for cutting the material into trapezoidal membranes.

DETAILED DESCRIPTION OF THE PREFERRED EMBODIMENTS

Figure 1:
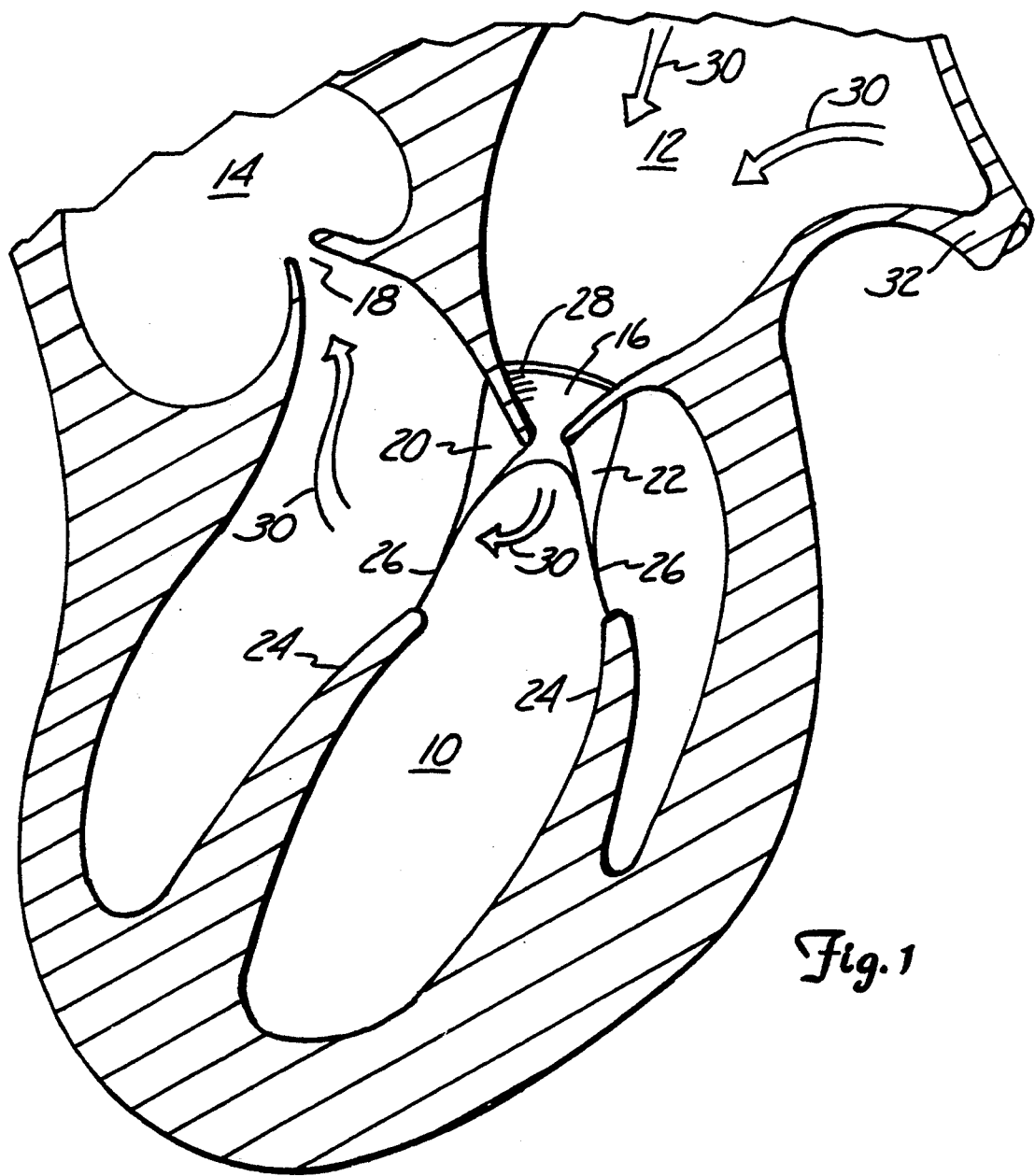
FIG. 1 is a section view of a portion of a human heart illustrating the position of the mitral valve.
Figure 2A:
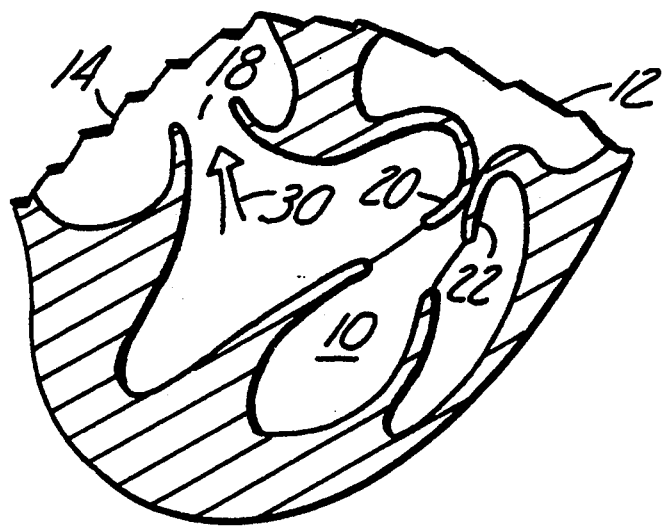
FIGS. 2A and 2B are section views as in FIG. 1 illustrating the function of the mitral valve during systole and diastole, respectively.
Figure 2B:
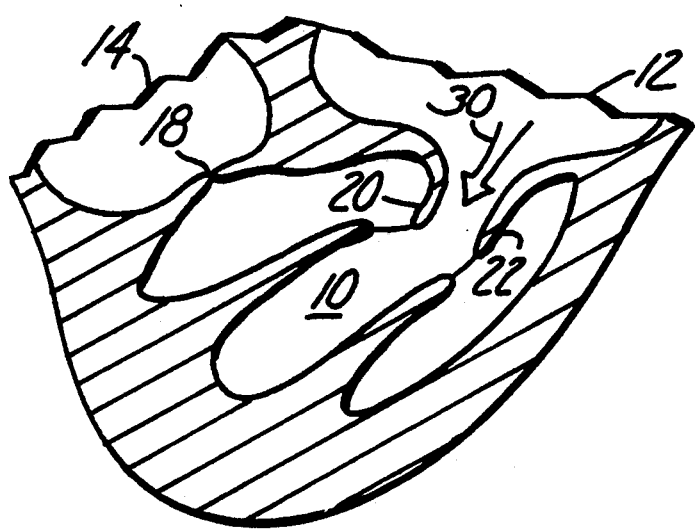

Referring to FIG. 1, there is illustrated a section of a portion of the human heart showing the left ventricle 10, left atrium 12 and aorta 14. Mitral valve 16 permits the flow of blood from the left atrium to the left ventricle, and aortic valve 18 permits flow from the left ventricle to the aorta. Mitral valve 16 includes an anterior leaflet 20 and a posterior leaflet 22. The apical zones of the leaflets are connected to papillary muscles 24 by chordae tendineae 26. The circumference of the mitral valve 16 is connected to about two-thirds of the circumference of the atrio-ventricular ring 28 and to the base of the aorta just below aortic valve 18. The primary flow of blood into the left ventricle is in the direction of arrows 30 from the pulmonary veins 32, through the left atrium 12, mitral valve 16 and into the left ventricle 10. The blood exits the left ventricle through aortic valve 18 to the aorta 14. As shown in FIG. 2A, during the contraction or systolic phase, pressure within the left ventricle forces aortic valve 18 open and forces the anterior and posterior leaflets 20 and 22 to coapt to close the mitral valve, thus forcing blood from the left ventricle in the direction of arrow 30 into the aorta 14. As shown in FIG. 2B, during the relaxation or diastolic phase, aortic valve 18 closes and the leaflets 20 and 22 of the mitral valve 16 separate to permit blood to flow into the left ventricle. Near the end of the diastolic phase, leaflets 20 and 22 begin to float upwardly toward the annulus to initiate closure of the mitral orifice and re-initiate the systolic phase.

Figure 3A:
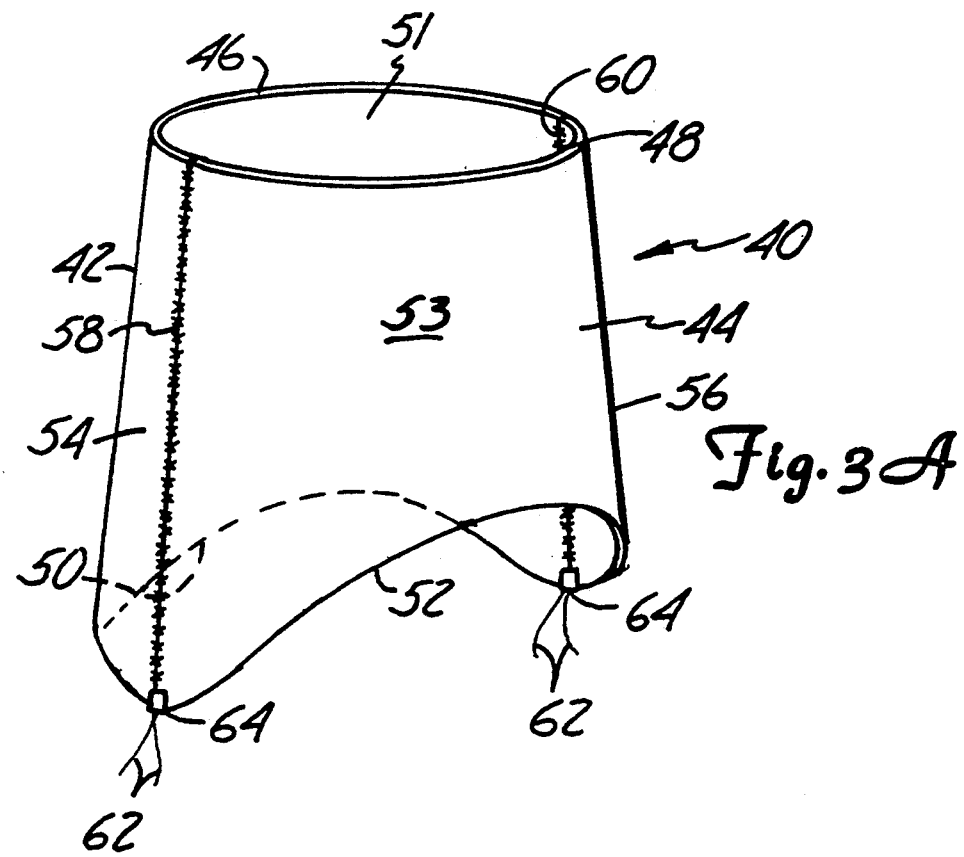
FIG. 3A is a prospective view of a mitral valve in accordance with the presently preferred embodiment of the present invention.

FIG. 3A illustrates a substitute mitral valve 40 in accordance with the presently preferred embodiment of the present invention. Valve 40 comprises a pair of trapezoidal membranes 42 and 44 which may be formed of a biocompatible synthetic fiber, such as Dacron, Teflon, PTFE, Goretex, polyurethane, or a natural tissue of human or animal origin, such as autologous, homologous or heterologous pericardium, dura mater, venous tissue, fascia (rectus abdominis, diaphragm, fascia lata), pleura, peritoneum. One end 46, 48 of membranes 42 and 44 forms an oval rim portion, whereas the opposite end includes an elliptical scallop 50, 52, respectively. The scallops form apical end portions 54 and 56 at the edges of each membrane so that when the membranes are sutured, as at 58 and 60, the flap portions form opposing flaps. As shown particularly in FIG. 4, the scallops are of equal width and unequal depth so that leaflets 51 and 53 (formed between each scallop and the respective rim) are of unequal size. The larger of the two leaflets (smaller scallop) is the anterior leaflet 51 for the valve, and the smaller of the two leaflets (larger scallop) is the smaller posterior leaflet 53.

Figure 4:
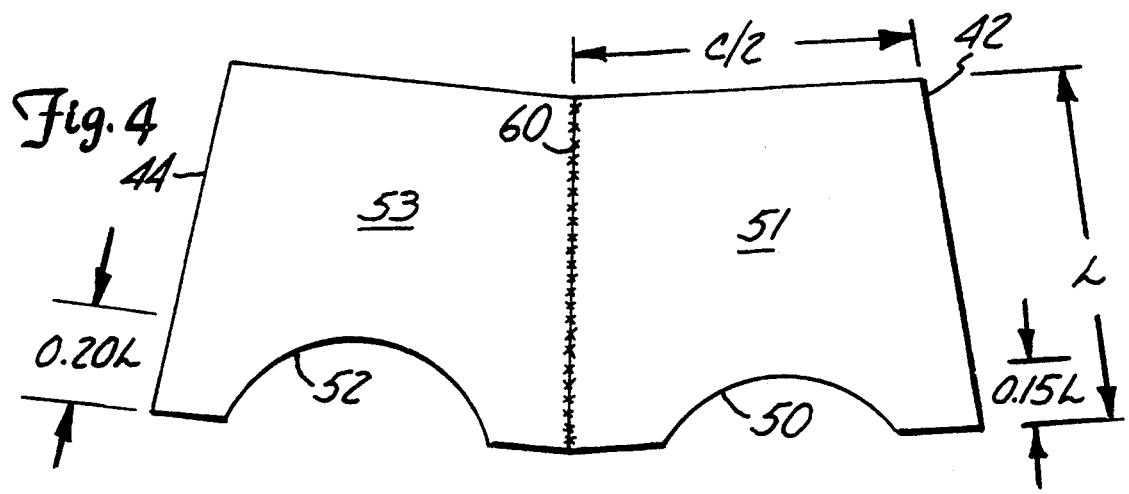
FIG. 4 is a plan view of trapezoidal membranes for construction of the valve illustrated in FIG. 3A.

As shown in FIG. 4, each leaflet has a trapezoidal shape with the top of the trapezoid being equal to C/2, where C is the circumference of the mitral ring. The height of each leaflet forms the length L of the valve and is equal to C/2. The long base of each leaflet is equal to 0.6 C, or about 1.2 times the length of the short base. The scallop is centered on the base and has a width of 0.4 C, leaving apical zones for each leaflet equal to 0.1 C. It will be appreciated that upon joining leaflets, the apical zones attached to the papillary muscles by the chordae tendineae will have a width of about 0.2 C.

The depths of scallops 50 and 52 are chosen to assure proper operation of the valve; the depths being deep enough as to provide good opening and flow characteristics, but not so deep as to exhibit poor closing characteristics. I have found that a depth of 15% of the height (0.15 L) of the leaflet for the anterior leaflet and 20% of the height (0.20 L) of the leaflet for the posterior leaflet provide good operating characteristics for the resulting valve. If the valve is manufactured in a central laboratory, the valve is tested for optimum operating characteristics (flow, opening and closing) before being supplied to the surgeon. If the valve and scallop profile are to be finished by the surgeon, the surgeon will cut openings at the positions where the scallops will be formed, and the valve is tested for opening, flow and closing characteristics. The tests are repeated with deeper openings until optimum operating characteristics are achieved. The elliptical scallops 50 and 52 are cut into the membranes to the depths of the openings, thereby forming the finished valve. Conveniently, the surgeon is provided with cutting dies according to the present invention to form the scallops.

Membranes 42 and 44 are joined together with double continuous 2-0 (Goretex) sutures with the inferior end of each suture buttressed between two small pledgets 64 of Teflon. The free ends 62 of the sutures are left uncut for attachment to the papillary muscles 24 (FIG. 1). The membranes are prepared in a sterile environment, cut to size and stored in preservation solutions in sealed plastic or glass jars. The jars are labelled in accordance to size of the membranes and size and position of elliptical scallops. For a mitral valve formed of homologous or heterologous pericardium, prior to the replacement procedure the pericardium is washed in saline and fixed in a 0.2 to 0.7 percent solution of purified glutaraldehyde (A 280 nm/A 230 nm>3) prepared in non-phosphate buffer, pH 7.4 for fourteen days. Preferably, the solution is enriched with known solutions (such as magnesium) for anticalcification purposes. Alcohol, glycerol, polyglycil ether or other suitable solutions may also be used. The valve or valve pieces are stored in a suitable preservative, such as 4% formaldehyde in 0.2M acetate buffer. Prior to insertion, the valve or valve pieces, such as the pericardium pieces, are washed in a saline solution to remove the preservation solution.

Under cardio-pulmonary bypass conditions, the left atrium is opened and the diseased mitral valve excised, leaving a few millimeters of chordae tendineae above each papillary muscle. The circumference, C, of the mitral ring is measured (such as with an oval obturator), and the distance, D, is measured between the tip of the papillary muscle (at the point of insertion of the main chordae) and the mitral ring (at the point nearest the papillary muscle). The valve size is selected so that the circumference of the artificial valve equals the measured circumference, C, of the mitral ring, and the length L of the valve (FIG. 3) equals C/2. As a check on the length L of the valve, the surgeon will calculate the equivalent diameter, d, of the mitral ring from the circumference, C, and check that L approximately equals 115% of the measured distance between the mitral ring and the papillary muscle plus d/2. Thus, $L \approx 1.15(D+d/2)$. These dimensions can be selected from Table I.

TABLE I

| Measured and Calculated Sizes of the Graft | | | |
|---|---|---|---|
| Circumference (cm) | Diameter (cm. C × 0.318) | Area (sq. cm.) (sq. C × 0.07958) | Length (C/2) |
| 4.5 | 1.4 | 1.53 | 2.2 |
| 5 | 1.5 | 1.98 | 2.5 |
| 5.5 | 1.7 | 2.40 | 2.7 |
| 6 | 1.9 | 2.85 | 3.0 |
| 6.5 | 2.0 | 3.33 | 3.2 |
| 7 | 2.2 | 3.89 | 3.5 |
| 7.5 | 2.3 | 4.44 | 3.7 |
| 8 | 2.5 | 5.06 | 4.0 |
| 8.5 | 2.7 | 5.72 | 4.2 |
| 9 | 2.8 | 6.44 | 4.5 |
| 9.5 | 3.0 | 7.16 | 4.7 |
| 10 | 3.1 | 7.95 | 5.0 |
| 10.5 | 3.3 | 8.76 | 5.2 |
| 11 | 3.5 | 9.62 | 5.5 |
| 11.5 | 3.6 | 10.52 | 5.7 |
| 12 | 3.8 | 11.45 | 6.0 |
| 12.5 | 3.9 | 12.37 | 6.2 |
| 13 | 4.1 | 13.39 | 6.5 |

Normally, the lengths of the flaps are equal. In rare cases the distance between the mitral ring and the each papillary muscle is different, in which case the surgeon will adjust the length of the flaps in accordance with the relationship $L=1.15(D+d/2)$.

The left ventricle continues to change in size throughout most of life. Consequently, it is important that any artificial valve compensate for change in size of the left ventricle, or re-operation will be required. The above relationship and Table I provide adequate dimensions for the artificial valve to reduce the likelihood of re-operation.

In the case of a replacement valve formed during the operation from autologous pericardium, the pericardium is preserved in a glutaraldehyde solution (0.5 to 25 percent) for between one and ten minutes. Cutting dies are chosen in accordance with the foregoing relationships for the calculated sizes of the graft and the inferior margins of the selected membranes are trimmed to a desired elliptical shape as shown in one of FIGS. 4A, 4B and 4C. The lateral edges of the membranes are sutured together with double continuous 2/0 (Goretex) sutures.

Figure 5A:
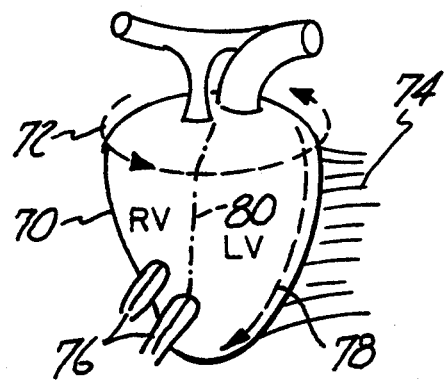
FIGS. 5A and 5B are views of a bovine pericardium which is mapped in accordance with the present invention for selecting and forming the trapezoidal membranes employed in the valve of FIG. 3A.
Figure 5B:
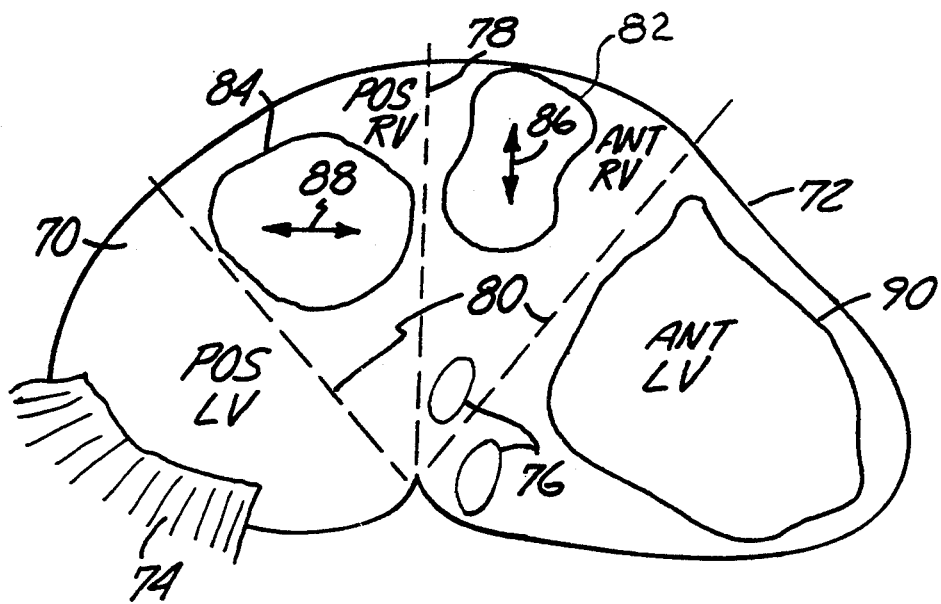

FIGS. 5A and 5B illustrate the technique for harvesting pericardium for construction of the leaflets illustrated in FIG. 4. The technique for harvesting pericardium will be described in connection with bovine pericardium, but it is understood that the techniques described herein are equally applicable to other animal and human pericardium, including donor pericardium. FIG. 5A illustrates the pericardium sac 70 surrounding the heart with dotted line 72 representing the base of the pericardium. The aorta, pulmonary arteries, pulmonary veins and other major veins and arteries are illustrated as emanating from the base of the pericardium. Muscle fiber 74 attaches the pericardium to the diaphragm adjacent the posterior side of the left ventricle. The anterior side of the pericardium is attached to the sternum by two sterno-periocardic ligaments 76. The pericardium sac is shown divided into four regions, the anterior and posterior regions being separated by dotted line 78 and the left and right ventricles being separated by dotted line 80. FIG. 5B shows the pericardium sac 70 laid out flat as if it had been cut along base line 72 and part of line 78. The right side of FIG. 5B illustrates the region of the anterior side of the left ventricle, and the left side of FIG. 5B illustrates the posterior side of the left ventricle.

Experimentation conducted on bovine pericardium revealed two areas 82 and 84 over the anterior and posterior regions of the right ventricle which exhibit superior tearing strengths, unidirectional fiber orientation and greater thicknesses than other regions of the pericardium. Regions 82 and 84 of bovine pericardium taken from twenty-two week old calves, exhibited thicknesses between about 0.45 and 0.65 millimeters, with the fibrous tissue being orientated predominantly in a direction indicated by arrow 86 in region 82, and in the direction of arrow 88 in region 84. The material in the regions 82 and 84 was found to exhibit the greatest resistance to tearing in directions indicated by the arrows 86 and 88. Another region, 90, predominantly overlying the anterior region of the left ventricle, was found also to be of significantly thick pericardium, but fiber orientation tended to be more mixed. Suture holding power for the regions 82, 84 and 90 were found to be higher than other regions, usually in the range between about 40 and 60 megapascals (MPa).

Where pericardium is used for construction of a mitral valve according to the present invention, it is preferred that the pericardium be harvested from the regions 82 and/or 84. Although bovine pericardium is specifically described, it is believed human pericardium exhibits similar characteristics and that the preferred region of harvest is the regions 82 and 84 adjacent the right ventricle. Hence, donor pericardium may be employed in constructing the valve.

The valve may be constructed by excising pericardium from the regions 82 and 84, selecting cutting dies for cutting the pericardium in accordance with the sizes described above, orienting the cutting dies so that the fibrous orientation of the pericardium is orientated generally along the dimension L in FIG. 4 (between the rim of the intended mitral valve and the apical ends to be attached to the papillary muscles), and cutting the pericardium into the individual trapezoidal shape, with elliptical scallops, as previously described. The trapezoidal membranes are sutured along their edges, as at 58, to form the mitral valve illustrated in FIG. 3A.

More particularly, a kit may be provided containing a plurality of pairs of cutting dies each having cutting edges arranged to sever pericardium into the sizes and shapes of membranes 42 and 44 in FIG. 4. Hence, each die of each pair has a generally trapezoidal shape with a short base length selected by the surgeon equal to one-half the measured circumference of the mitral ring. The length L, along one edge of the membrane is equal to the length of the short base, the long base is equal to 1.2 times the length of the short base, and the elliptical scallop has a width equal to 0.8 times the short base and is centered on the long base. The depth of the scallop for one die of each pair is 0.15 times the length, whereas the depth of the scallop for the other die of each pair is 0.20 times the length. Each pair of dies is selected for a different nominal circumference of the mitral ring, as set forth in table I.

Figure 3B:
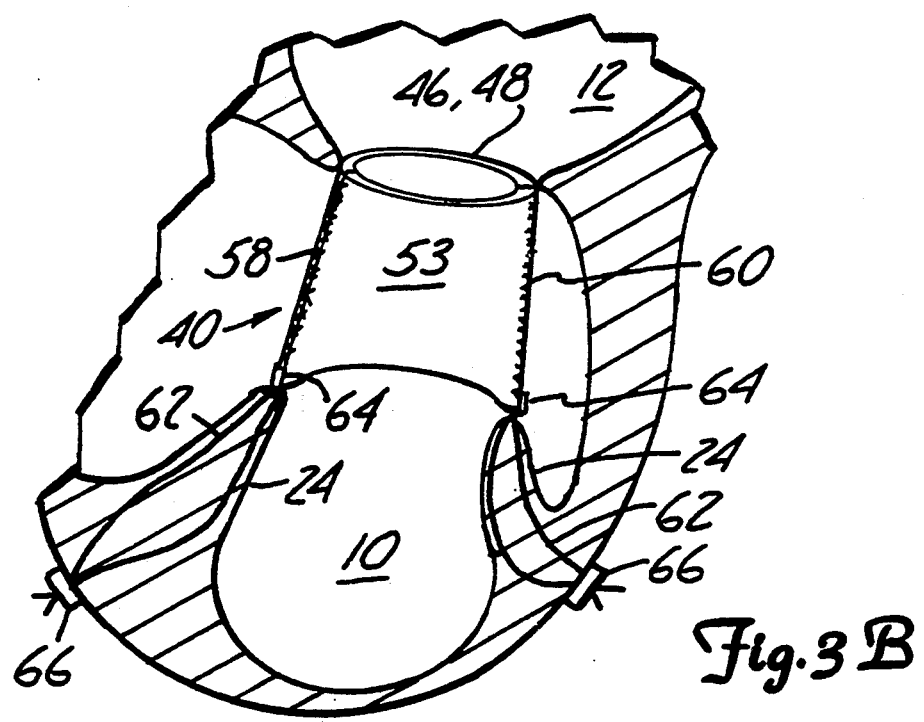
FIG. 3B is a view illustrating the manner of implanting the valve illustrated in FIG. 3A.

FIG. 3B illustrates the technique for inserting the substitute valve. The substitute valve 40 is lowered into the left ventricle so that the uncut sutures 62 of each of the sutures 58 and 60 are attached to the tip of each papillary muscle with a figure "8" suture. A 2/0 Goretex suture is passed through the Teflon pledget 64 at the end of each flap portion in a U-shaped fashion and is inserted on the endocardial surface of each papillary muscle and passed through the left ventricular wall. The sutures are tied on the outside of the epicardial surface with Teflon pledgets 66, avoiding major coronary vessels. Prior to tying, the sutures are pulled straight without tension. The stitch is designed to secure attachment of the replacement valve at the papillary muscle in case other sutures break loose.

The papillary muscle will be used for operation of the replacement valve. Consequently, it is preferred that the sutures are not passed through the core of the papillary muscle, as has been done in previous procedures, so as to avoid damage to the vessels and integrity of the muscle.

The rim 46, 48 of the replacement valve is then pulled up to the mitral ring. The size is again checked, and the superior circumference of the replacement valve is sutured with a circular continuous 2/0 (Goretex or polyester) suture to the annulus and to any remnants of the excised mitral valve. Isolated sutures may be used for positioning the replacement valve.

Sutures 58 and 60 along the length of flaps 54 and 56 of the replacement valve serve four important functions. First, they serve as reinforcement in a manner similar to the tendon fibers in the natural valve to transmit force from the ventricle through the papillary muscle to the mitral ring and thence to the fibrous trigon of the heart. Hence, the sutures 58 and 60 support much of the stress through the valve. A second function of the two-piece sutured membrane valve permits the selection of the pericardium membranes and their arrangement so that the longitudinal fibers may be aligned with the papillary muscles. This provides greater strength and reliability to the replacement valve. A third function of the two-piece sutured valve is that the pericardial tissues are selected for the differences between the anterior and posterior leaflets, thereby providing greater simulation of the natural valve. A fourth function of the two-piece valve is that the double suture technique assures that the replacement valve is a bicuspid valve, allowing the tissue between the suture lines on both flaps to form the leaflets which coapt and provide the principal mechanism of opening and closure of the valve. Thus, when the leaflets coapt, they do so with less folding and more uniform closure than in prior unsupported replacement valves. Each leaflet operates to close or obturate half of the mitral orifice during left ventricle systole. The trapezoidal shape of the valve membranes assures that the lower orifice of the valve is larger than the upper orifice (or opening). This assures better flow through the valve than in cylindrical valves, with no pressure gradient across the lower orifice.

The cardiac valve according to the present invention may be assembled by the surgeon during the procedure from a selection of membranes, or from a tissue of two assembled membranes, or from the patient's pericardium. It is preferred, however, that the valve be fully completed at a central processing laboratory to assure control over the forming and suturing of the membranes.

The present invention thus provides an effective artificial cardiac valve which closely simulates the function and operation of the natural valve. The valve cooperates with the papillary muscles to closely simulate the action of the natural valve during systole and diastole. The high ratio of effective orifice area to mitral ring dimensions gives the valve according to the present invention superior hydrodynamic and hemodynamic characteristics in comparison to prior valves. The valve is sized to remain competent and functional to changes in size of the left ventricle and of the orifice to which the valve is attached; the length of the graft and leaflets provide sufficient substance for coaptation regardless of expected changes in the distance between the mitral ring and papillary muscles. Anticoagulation treatment is not expected to be required, and tissue treatment effectively prevents later calcification.

Although the present invention has been described in terms of a bicuspid valve, such as a mitral valve, it is understood that the same principles may be applied to other cardiac valves, including the aortic, tricuspid and pulmonary valves, without departing from the spirit or scope of the present invention. Further, although the present invention has been described with reference to preferred embodiments, workers skilled in the art will recognize that changes may be made in form and detail without departing from the spirit and scope of the invention.

What is claimed is:

1. A cardiac valve comprising a plurality of flexible membranes, each membrane having edges and first and second ends, strengthening means joining the edges of adjacent ones of said membranes to form an unsupported body, said first ends together forming an oval end of said body, and said second ends forming a plurality of free apical ends of said body, each apical end being integral to the body and having a length to permit direct attachment to papillary muscles of a recipient, said body having a pair of oppositely-disposed flexible flaps integral with and extending from said oval end and between the apical ends and arranged to coapt during systole to close the valve and to separate during diastole to open the valve, said strengthening means extending between each apical end and the oval end to support force between the papillary muscles and the oval end.

2. A cardiac valve according to claim 1 wherein the flaps are formed by a plurality of substantially parabolic scallops formed in said second end, one of said scallops being formed in each of said membranes, said scallops said free apical ends.

3. A cardiac valve according to claim 2 wherein said scallops have relatively different sizes.

4. A cardiac valve according to claim 3 wherein the oval end has a circumference C and each membrane has a length between its first and second ends approximately equal to C/2.

5. A cardiac valve according to claim 4 wherein said membranes are joined by sutures along each edge from said oval end to an apical end.

6. A cardiac valve according to claim 1 wherein said flaps are formed by a substantially parabolic scallop in the second end of each membrane, and said membranes are joined along each edge from said oval end to the apical end.

7. A cardiac valve according to claim 1 wherein there are two flaps forming a bicuspid valve, the oval end has a circumference C and each membrane has a length between its first and second ends approximately equal to C/2.

8. A cardiac valve according to claim 1 wherein the edges of the membranes are joined by sutures to support stress on said body imposed by a papillary muscle.

9. A cardiac valve according to claim 1 wherein each of said membranes is trapezoidal and the edges of the membranes are joined to form a frusto-conical body.

10. A cardiac valve having a closed body of flexible unsupported tissue, said body having an oval end, a pair of oppositely-disposed flexible flaps extending from said oval end and a pair of free apical ends, the apical ends being integral to the body and having a length to permit direct attachment to papillary muscles of a recipient, the flaps coapting during systole to close the valve and separating during diastole to open the valve, and strengthening means attached to the body and extending between each apical end and the oval end to support force between the papillary muscles and the oval end.

11. A cardiac valve according to claim 10 wherein said strengthening means comprises sutures.

12. A cardiac valve according to claim 10 wherein said strengthening means is arranged to support stress on said body imposed by a papillary muscle.

13. A cardiac valve according to claim 10 wherein the closed body is a frusto-conical body.

14. A method of forming an unsupported artificial cardiac valve intended to replace a native valve attached to a circumferential valve ring and papillary muscles of a recipient comprising:

selecting first and second flexible membranes each having opposite edges, a first end forming a continuous rim between said edges and a second end opposite the first end, an elliptic scallop formed in the second end of each membrane to form first and second flexible half-flap portions at the edges of the respective membranes, said half-flap portions forming a pair of free apical ends at the second end of the membranes when the edges of the first membrane are attached to the edges of the second membrane, the apical ends being integral to the membranes and having a length to permit direct attachment to the papillary muscles of the recipient; and fastening the edges of said membranes together with a strengthening means to form a closed body so that the first ends of the membranes together form a rim having a circumference approximately equal the circumference of the native valve ring, the body coapting during systole to close the valve and separating during diastole to open the valve, the strengthening means extending from each free apical end to the rim to support force between the valve ring and the papillary muscles.

15. The method according to claim 14 wherein the first and second membranes each has a length between its respective first and second ends, and further including adjusting the length of the membranes to be equal to C/2, where C is the circumference of the native valve ring.

16. The method according to claim 14 wherein the scallop formed in the first membrane has a different size from the scallop formed in the second membrane.

17. The method of claim 14 further including harvesting pericardium tissue from a region of a pericardium sac of a mammal donor located adjacent an anterior side or posterior side of a right ventricle of the donor, the harvested pericardium tissue having predominately aligned fibers, and forming the first and second membranes from the harvested pericardium tissue so that the fibers within the tissue are substantially aligned along the length of the valve between the first and second ends.

18. The method of claim 14 wherein the first and second membranes are trapezoidal and the edges of the membranes are joined to form a frusto-conical body.

* * * * *

UNITED STATES PATENT AND TRADEMARK OFFICE
CERTIFICATE OF CORRECTION

PATENT NO. : 5,344,442

DATED : September 6, 1994

INVENTOR(S) : RADU DEAC

It is certified that error appears in the above-indentified patent and that said Letters Patent is hereby corrected as shown below:

Column 9, line 52, before "said free", insert —forming—

Signed and Sealed this

Thirty-first Day of January, 1995

Attest:

BRUCE LEHMAN

*Attesting Officer*  *Commissioner of Patents and Trademarks*